US006849076B2

(12) United States Patent
Blunn et al.

(10) Patent No.: US 6,849,076 B2
(45) Date of Patent: Feb. 1, 2005

(54) SURGICAL DISTRACTION DEVICE

(75) Inventors: Gordon Blunn, North Hertfordshire (GB); John Perry, Hertfordshire (GB); Hilali Noordeen, London (GB); Jay Meswania, Hertfordshire (GB); Justin Cobb, London (GB)

(73) Assignee: University College London, London (GB)

( * ) Notice: Subject to any disclaimer, the term of this patent is extended or adjusted under 35 U.S.C. 154(b) by 36 days.

(21) Appl. No.: 10/257,260

(22) PCT Filed: Apr. 12, 2001

(86) PCT No.: PCT/GB01/01668

§ 371 (c)(1),
(2), (4) Date: Jan. 28, 2003

(87) PCT Pub. No.: WO01/78614

PCT Pub. Date: Oct. 25, 2001

(65) Prior Publication Data
US 2004/0030395 A1 Feb. 12, 2004

(30) Foreign Application Priority Data

Apr. 13, 2000 (GB) .............................................. 0009107

(51) Int. Cl.⁷ .............................. A61F 17/56; A61F 2/00
(52) U.S. Cl. .......................... 606/105; 606/53; 606/57; 606/63; 606/60; 623/11.11; 623/18.12; 623/23.45
(58) Field of Search ............................ 606/105, 53–63; 623/18.12, 11.11, 23.45

(56) References Cited

U.S. PATENT DOCUMENTS 3,873,066 A  *  3/1975  Opyrchal ..................... 254/103
3,976,060 A  *  8/1976  Hildebrandt et al. ........ 606/241
4,370,091 A  *  1/1983  Gagliardi ..................... 414/735
4,931,055 A      6/1990  Bumpus et al.
5,334,202 A  *  8/1994  Carter .......................... 606/58
5,364,396 A     11/1994  Robinson et al.
5,429,638 A  *  7/1995  Muschler et al. ............. 606/60
5,626,579 A  *  5/1997  Muschler et al. ............. 606/60
5,704,939 A      1/1998  Justin
6,245,075 B1     6/2001  Betz et al.

FOREIGN PATENT DOCUMENTS

| DE | 24 37 752 A1 | 2/1976 |
| EP | 0 548 535 A1 | 6/1993 |
| WO | 99/51160 | 10/1999 |

OTHER PUBLICATIONS

O.S. Schindler, MD, "Stanmore Custom–Made Extendible Distal Femoral Replacements", Clinical Experience in Children with Primary Malignant Bone Tumours, Royal National Orthopaedic Hospital, Stanmore, England, 1997 British Editorial Society of Bone and Joint Surgery, vol. 79–B, No. 6, Nov. 1997.

* cited by examiner

Primary Examiner—David J. Isabella
(74) Attorney, Agent, or Firm—Burns, Doane, Swecker & Mathis, L.L.P.

(57) ABSTRACT

A surgical distraction device is provided for applying extending or tensioning force non-invasively to a patient's skeleton or to an implant which comprises anchoring means for attaching first and second components of the device to a bone or to adjoining bones, said components being connected by a linkage of an extendible length, a magnet connected to the linkage via a reduction gearbox and actuating means located externally of the patient for generating a moving or varying electro-magnetic field, thereby causing the magnet to rotate and the linkage to be extended.

13 Claims, 6 Drawing Sheets

SURGICAL DISTRACTION DEVICE

This invention relates to surgical distraction devices and in one form provides a surgical distraction device for exerting an extending or tensioning force to bones and/or implants within a patient's skeleton.

In the treatment of malignant bone cancer it is often necessary to surgically resect part of a bone and to replace it with a prosthesis. Where the patient is a child or adolescent, the skeleton continues to grow and in order to accommodate this the prosthesis requires replacement at intervals. In an effort to reduce the number of revision operations, procedures have been developed for extending the prosthesis in situ. Methods of achieving this include the provision of telescopic parts in the prosthesis which are extended by introducing spacers of approximate size between the parts. Devices which have been used for this purpose are described in the paper by Schindler et al, the Journal of Bone and Joint Surgery, Volume 79b, No. 6, November 1997, pages 927 to 937.

While the system described in the above paper is preferable to repetitive revision operations, it still requires surgical access to a part of the prosthesis at intervals which can be frequent, depending on the growth rate of the patient. Since all operations carry finite risks, including the risk of introducing an infection, it is one object of this invention to provide a device which can be used to extend a prosthesis non-invasively.

According to one aspect of the present invention there is provided a surgical distraction device for applying an extending or tensioning force non-invasively to a patient's skeleton which comprises anchoring means for attaching first and second components of the device to a bone or to adjoining bones, said components being connected by a linkage of variable length, a magnet connected to the linkage via a reduction gearbox and means located externally of the patient for generating a moving or varying electromagnetic field, thereby causing the magnet to rotate and the linkage to be varied in length.

In practice, the first and second components and its associated linkage, together with the magnet, are surgically introduced and anchored to the bone or bones, for example when fitting a prosthesis or implant.

At intervals when the device requires extension or tensioning, a moving electric field is established around the patient's body in the region of the prosthesis or implant, thereby causing the two components to be pressed apart. Normally, the magnetic field is arranged to rotate in the direction of desired movement of the magnet connected to the linkage.

According to a second aspect of the invention there is provided an extendable endoprosthetic replacement device which comprises first and second components which are connected by a linkage of extendable length, the first component comprising a component of a limb joint and the second component having means for attachment to a resected long bone, a magnet connected to the linkage and means adapted for location externally of the patient for generating a moving electromagnetic field, thereby causing the magnet to rotate and the linkage to be extended.

The distraction device in accordance with the invention has substantial advantages over existing practices such as described in the paper cited above, since it avoids the trauma of further surgical operations, reducing the risk of infection and the introduction of further scar tissue as a result of the operations. Moreover, the device can be extended or tensioned over a longer period than might be practical in the course of a surgical operation. The device can also be extended more gradually and more frequently, which induces an expansion or tensile force, which keeps pace with growth and stimulates biological growth of tissues.

The provision of a reduction gearbox between the magnet and the relatively movable components of the distraction device carries with it important advantages. First it enables a uniform extension force to be applied to the extensible components. Secondly it enables sufficient force to be applied to overcome resistance to extension and to resist any tendency for the device to contract in length when the bone is loaded.

Although a major use of the device in accordance with the invention is the periodic extension of prostheses for the reasons described in the paper cited above, there are a number of other surgical purposes for which the device is of value. One of these is in distraction osteo-genesis. This treatment involves tensioning of bone in order to stimulate its growth The conventional procedure involves provision of an external frame, e.g. around a limb and pins are anchored to the bone at a spaced distance. Tensioning rods are then fitted between the pins in order to apply a constant tensioning force to the bone. These devices are extremely cumbersome and awkward for the patient, often making it difficult or impossible for the patient to walk. In addition, there is a considerable risk of infection caused by the use of transcutaneous pins. With the device of the present invention, it can be surgically introduced and the components anchored to the bone and tensioning can be applied either continuously or at intervals by placing the means for generating the rotating electromagnetic field around the implanted device.

The device also has application for curing curvature of the spine (scoliosis). In this procedure, the components of the device will be anchored to appropriate vertebrae or to a rib and selected vertebrae. The distraction force is applied using an externally generated electro-magnetic field to overcome the resistance of the tissue of the limb, together with the friction of the linkage. Use of the device is not limited to applying distraction forces to bone but could, in a modified form, be used for attachment to tendons and thereby used, e.g. for treating cerebral palsy.

According to a further aspect, therefore, there is provided a surgical distraction device for correcting curvature of the spine which comprises first and second extension rods, each having attachment means at one end for fixing to a respective vertebra, a linkage for linking the rods so that the ends carrying attachment means are relatively moveable, said linkage being connected to a drive mechanism comprising a rotatable magnet and a reduction gearbox and actuating means for location externally of the patient for generating a moving or varying electric/magnetic field, thereby causing the magnet to rotate and the attachment means on one rod to move relatively to the attachment means on the other rod.

One embodiment of the present invention will now be described with reference to the accompanying drawings, in which.

Figure 1:
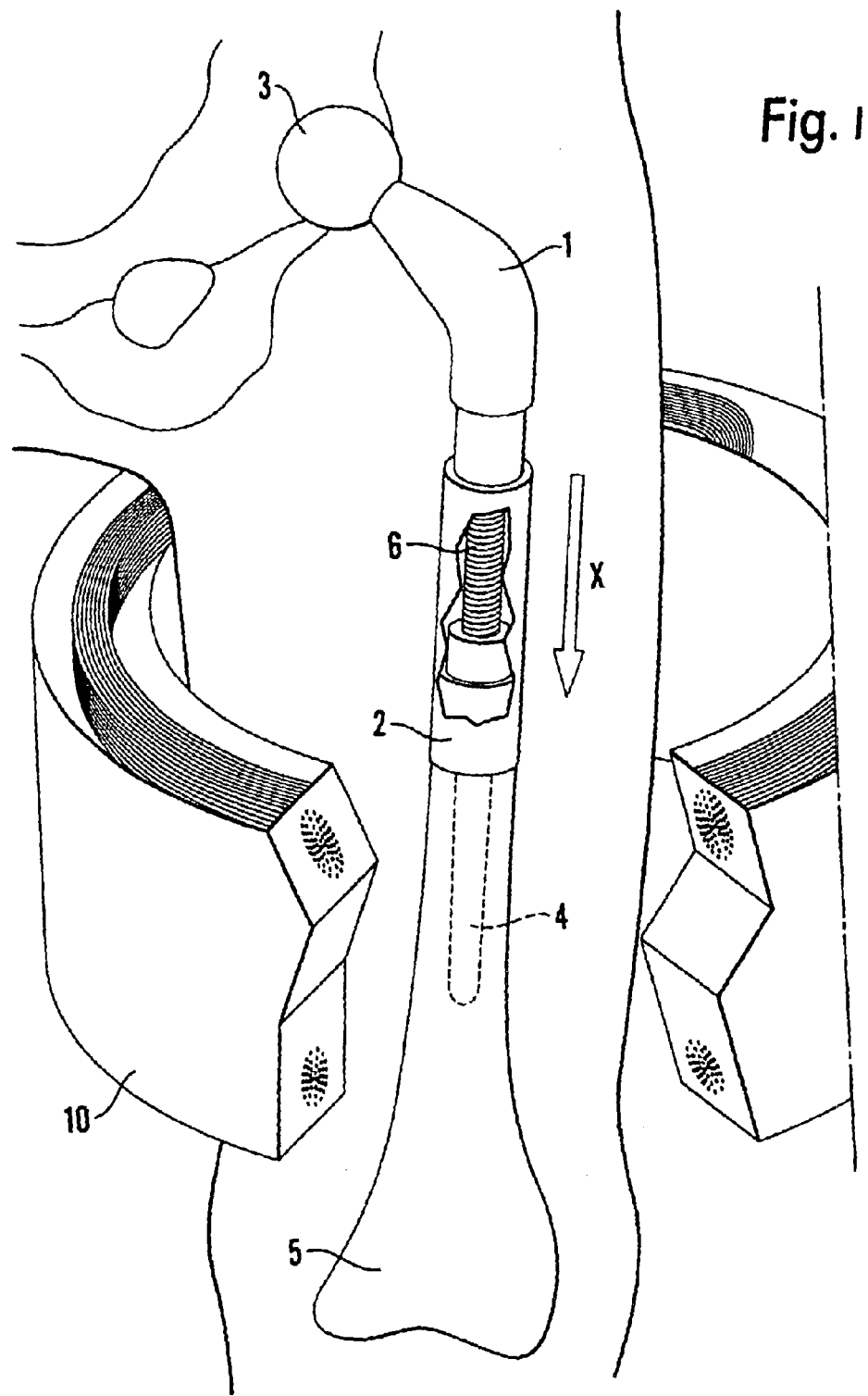
FIG. 1 is a perspective view of the distraction device fitted to a femur and forming part of a femoral prosthesis.

Referring to the drawings, the distraction device comprises two components, a first component (1) forming part of a femoral hip prosthesis including a ball joint (3), forming an artificial hip joint and a relatively moveable component (2) carrying a spigot (4) for anchorage to the re-sected femur (5). The components (1) and (2) are linked together by a linkage comprising an elongated screw (6) and a nut (7). Relative movement of the linkage axially in the direction of the arrow X is achieved by a rotatable magnet (8) connected to a gearbox (9). Magnet (8) is connected through the gearbox (9) to the spindle screw (6) and rotation of the magnet (8) causes rotation of the screw and hence elongation of the device.

Rotation of the magnet is achieved by placing an electromagnetic coil (10) around the limb and generating a moving electrical field. The magnet is designed so that the moving electric field causes the magnet to rotate in the desired direction, to cause extension of the device, the magnet and the electromagnetic coil together constituting an electrical motor. In general the electromagnetic coil takes the form of a ring of coils which may be incorporated or embedded in a magnetically susceptible material, e.g. soft iron, the ring being dimensioned to fit around the limb which contains the extendable distraction device.

The gearbox is a high reduction ratio gearbox which may have a reduction ratio in the order of several hundred, e.g. about 500. This ratio, the speed of rotation of the magnet and the pitch of the screw is selected so that, preferably, one turn of the rotor will advance the screw by a fraction of a millimetre, e.g. 0.001 to 0.01 mm, typically about 0.005 mm. The patient can remain within the electromagnetic coil for an extended period, e.g. one to two hours, depending upon the amount of extension or length of distracting force required.

In a procedure for lengthening a prosthesis, one would typically wish to extend the prosthesis by 5 to 6 mm at each stage. The distraction force should be such that it is capable of overcoming friction within the linkage and the resistance provided by soft tissue around the prosthesis.

Figure 3:
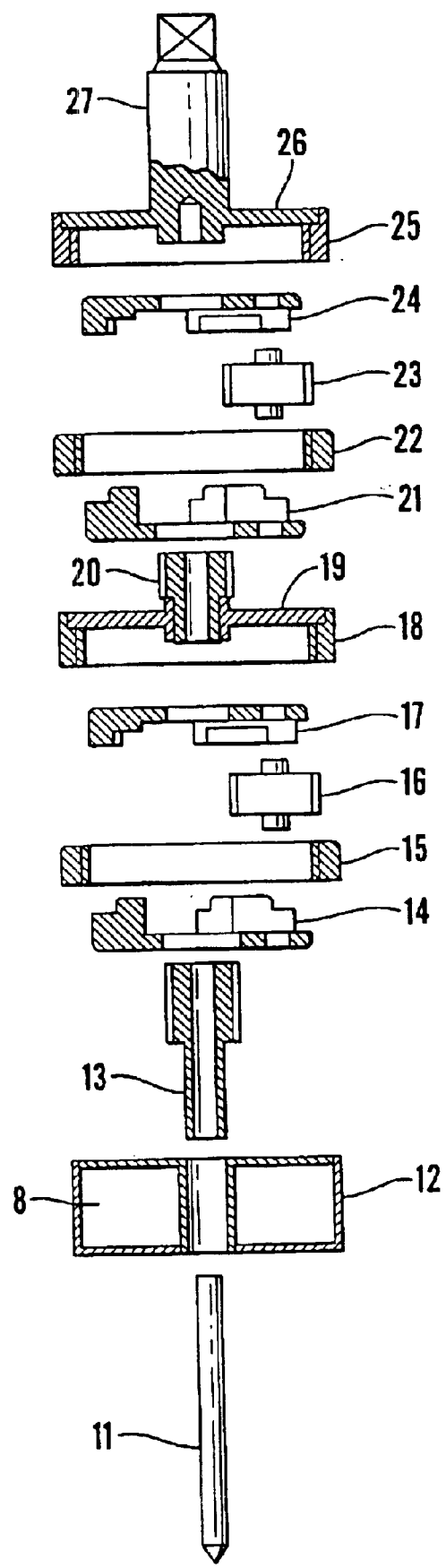
FIG. 3 is an exploded view of the gearbox.

FIG. 3 shows details of the gearbox. The gearbox incorporates two planetary gears and is sealed within a casing to exclude body fluids. The parts shown are all manufactured from stainless steel with the exception of the part (12) which is manufactured from titanium alloy and the part (26) which is manufactured from a cobalt chrome alloy.

Figure 2:
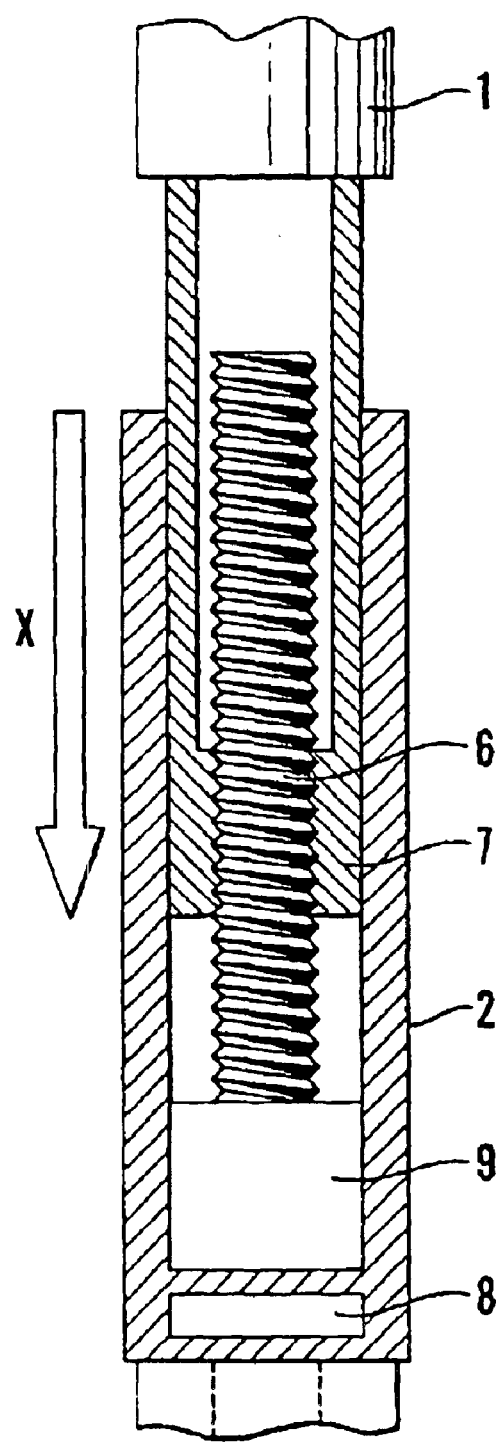
FIG. 2 is an enlarged, diagrammatic view showing the linkage between the two relatively extendible parts of the prosthesis.
Figure 2A:
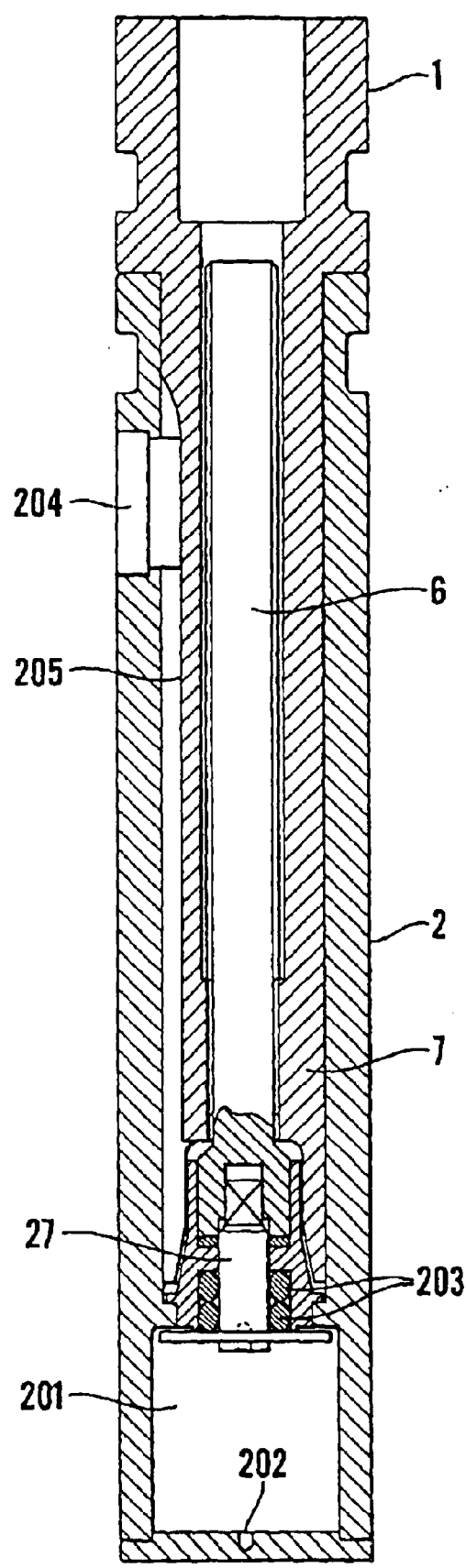
FIG. 2a is a view similar to FIG. 2 but showing the linkage in more detail.

The gearbox and magnet assembly are designed to be housed within a chamber (201) at the lower end of the linkage assembly (see FIG. 2a).

Reference numeral (11) shows an axial spindle on which the driving magnet rotates. The lower end of the spindle (11) is formed with a pointed portion so that the spindle is guided in a recess in the end cap (202—see FIG. 2a). Part (12) is a housing for containing the permanent magnet (8). The permanent magnet is preferably manufactured by a sintering process, has an annular shape and is fitted into an interlocking annular capsule (12) to ensure that the magnet will not rotate within the capsule.

After welding into the capsule (12) the magnet is magnetized with a field direction parallel to the diameter of the capsule (12). Part (13) is the input pinion to the first stage of the gearbox. The pinion is bored to be a free running fit on the spindle (1) and has a plane boss that is interlocked into the capsule (12). The components (14) and (17) are fitted together as a spigot and socket to form a planetary carrier assembly and planet gears (16) are fitted into the carrier assembly. Each gear stage has three identical planet gears which are fitted into the carrier assembly and each planetary gear is machined with a small integral stub shaft at each end. These stub shafts locate in holes in each half of the carrier assembly.

Components (15) and (22) are fixed internal gears for the first and second reduction stages respectively. These gears each mesh with approximately half of the face width of a set of planetary gears and are fixed into the body of a gearbox. The remaining half of the planetary gears is meshed with rotating internal gear (18). A reduction of the number of teeth in the rotating internal gear (18) compared with the number of teeth in the fixed internal gear (15) provides speed reduction for the stage. Higher number of reductions in the number of teeth provide a greater reduction using the minimum number of gears and space. Components (18), (19) and (20) comprise an assembly which transfers the output from the first stage of the gearing to the input of the second. The assembly comprises a gear web part (19) which is welded to both the rotating internal gear of the first stage of gearing and the input pinion of the second stage.

Parts (21), (22), (23), (24) and (25) comprise the fixed internal gear and planetary gear and carrier assembly for the second stage. These parts are the same as parts (14), (15), (16), (17) and (18) of the first stage of gearing.

Part (25) is the rotating internal gear of the second stage of the gearing and this is welded to part (26) which is the output shaft from the gearbox. This passes through O-ring seals (203) to drive the screw (6) shown in FIGS. 1, 2 and 2a.

Part (26) is a spigot fit into a socket machined into part (25) so that this assembly is self-jigging when set up for welding. This is the same arrangement as in the case of parts (18) and (19).

Part (26) is shown with a short spigot that locates in a bore in one side of the carrier (24). The purpose of this spigot is to ensure that the planet carrier is accurately centred in the mechanism and a similar spigot is provided on part (19) to centre the first stage planet carrier.

The upper face of part (26) carries an output shaft (27) which terminates in a suitably shaped drive projection engaging in a lead screw (6). Screw (6) is threadably received within an inner shaft (7). Outer shaft (2) surrounds inner shaft (7) so that inner shaft is extended out of shaft (2) when lead screw (6) is rotated by the magnet (8) driving through the reduction gearbox Inner shaft (7) is prevented from rotating by means of a key (204) which is fixed into a corresponding aperture in the outer shaft (7). Key (204) has a projecting portion which extends into a longitudinal slot (205) formed in the inner shaft (7).

The device may include an integral or separate sensor which counts the number of revolutions of the magnet (8) so that the degree of extension of the device can be monitored and/or recorded.

Figure 4:
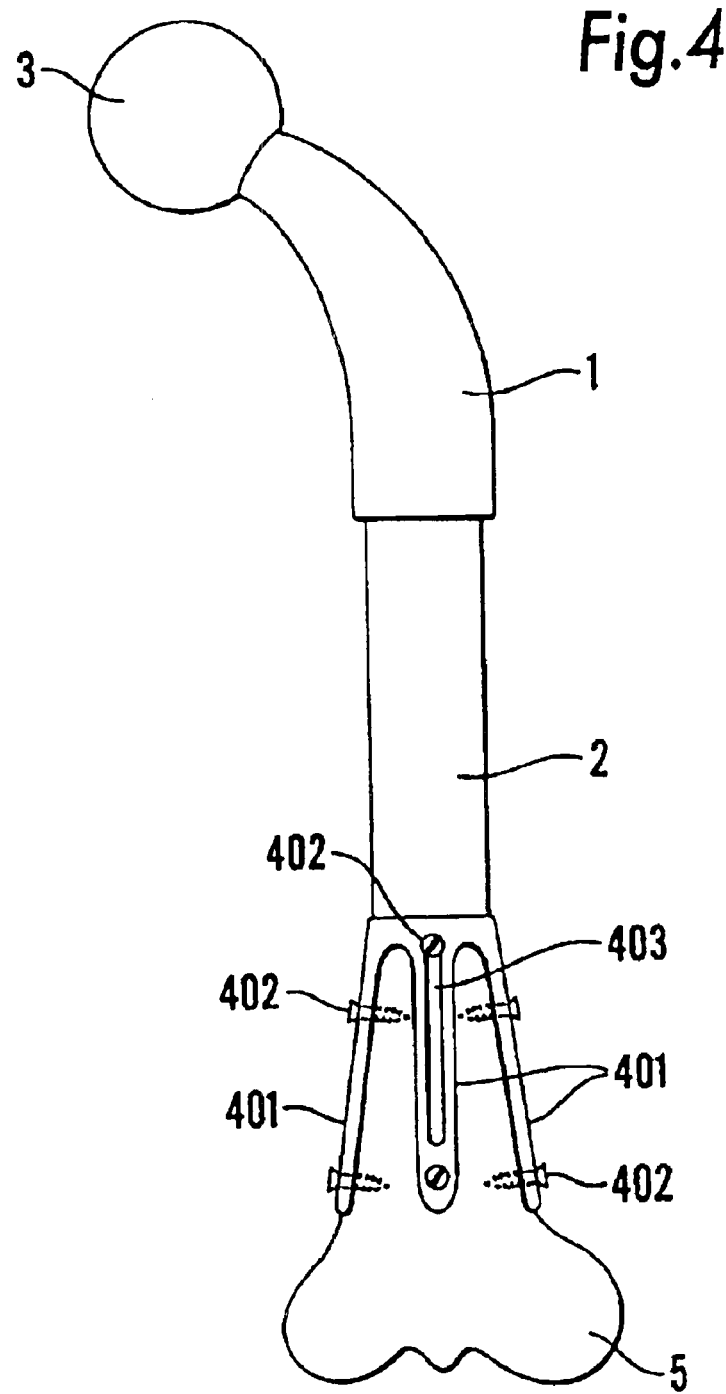
FIG. 4 illustrates an alternative method of fixing the prosthesis to a bone.

FIG. 4 illustrates an alternative method of anchoring one component of the device to a long bone, which has been found to result in improved stability and bone integration. As can be seen, the tubular body (2) of the prosthesis is fixed to a resected bone (5) by means of two or more plate-like strips (401) extending from the tubular body. The plate-like strips are apertured to receive unicortical screws (402) for fixing the plate-like strips to the outer surface of the bone. The strips were formed with elongated holes (403) to encourage bone ingrowth and coated with a highly crystalline hydroxyapatite coating to stimulate integration with the bone.

Figure 5:
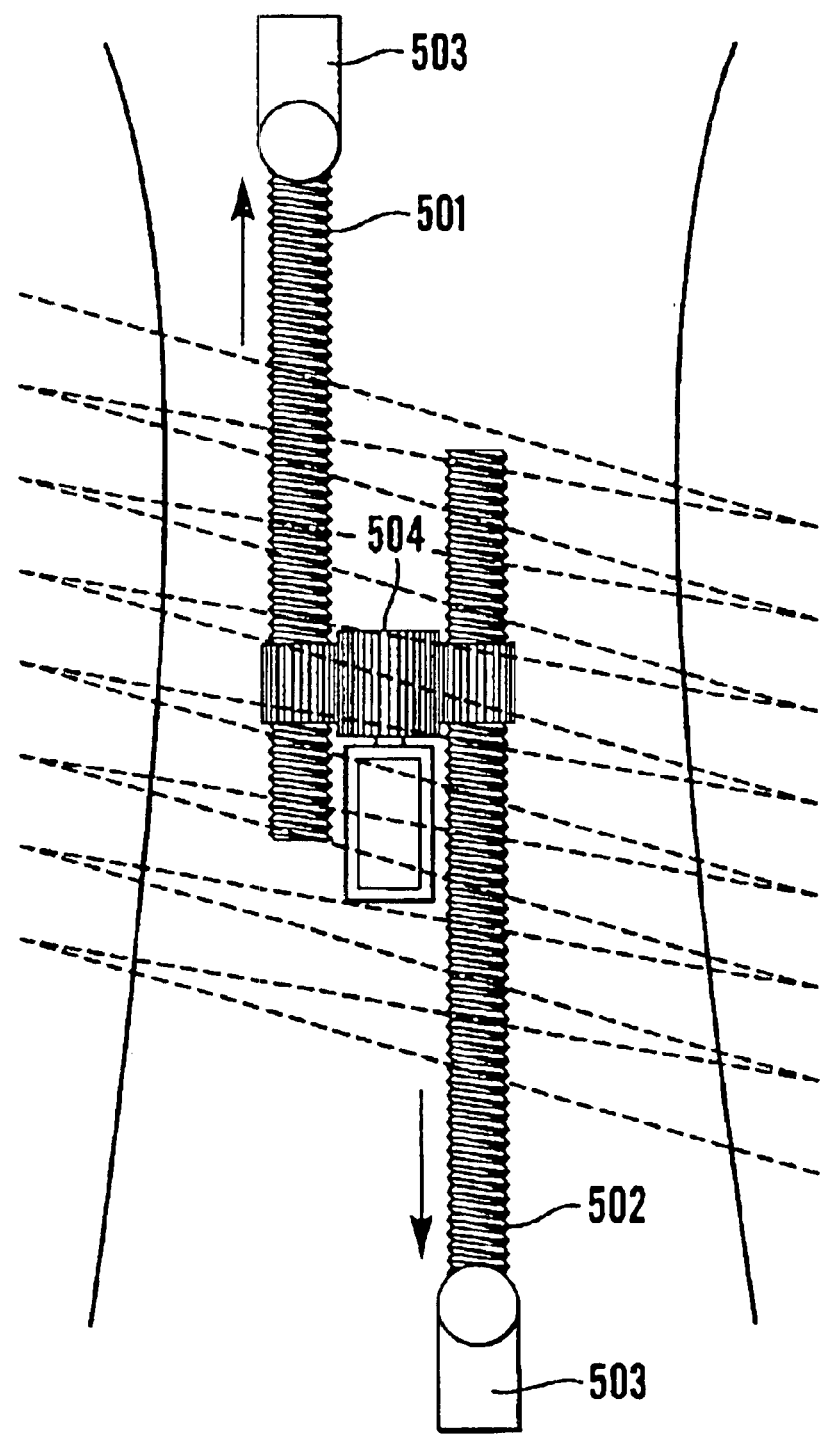
FIG. 5 is a perspective view of another embodiment of a distraction device for correcting curvature of the spine.

FIG. 5 shows a distraction device suitable for treatment of curvature of the spine. In this embodiment, threaded rods (501) and (502) are provided with attachment means (503), such as plates or blocks carrying screws or hooks. Depending on the curvature of the spine, the threaded rods (501) may be straight or curved. The attachment means may include a universal bearing or joint connection to the threaded rods so that the attachment means can be rotated or swivelled to take account of the curvature or deformation of the spine, and to enable firm attachments to be made to appropriate vertebrae.

The two threaded rods are joined by a central spacer or block (504). The block (504) may be stabilised by attachment to the spine, e.g. using screws or hooks. Block (504) includes a drive mechanism comprising a rotatable magnet and reduction gearbox as described in FIGS. 1 to 3. However, the final drive component comprises a cog carried by the output shaft. The cog is linked to two worm drives which are turned by the cog. In one arrangement, the worms are arranged in series such that they are driven in opposite directions. In another arrangement, the worms may be arranged to be driven in the same direction. Single worm or multiple worm drives of two or more worms may also be used to link the cog to the threaded rods. Each worm is cylindrical and has a central tapping. A corresponding threaded rod (502) is received within the worm and the threads on the rod match the tapping on the inside of the worm. As the worm is turned by the cog, the threaded rod is also turned and is moved in a direction lengthwise of the rod. The direction of movement of the rod depends on the sense of the cooperating threads and on the arrangement of the worms and gears which transmit the rotation of the magnet. In a similar way to the arrangement described in connection with FIGS. 1 to 4, a rotating electrical field is generated by means of an external annular coil around the patients' spinal region.

What is claimed is:

1. A surgical distraction device for applying an extending or tensioning force non-invasively to a patient's skeleton or to an implant which comprises anchoring means for attaching first and second components of the device to a bone or to adjoining bones, said components being connected by a linkage of an extendable length, a magnet connected to the linkage via a reduction gearbox having two or more gear reduction stages whereby the gearbox has a gear ratio of 100:1 or greater and actuating means located externally of the patient for generating a moving or varying electromagnetic field, thereby causing the magnet to rotate and the linkage to be extended.

2. A device according to claim 1, wherein the actuating means is adapted to generate a rotating magnetic field which rotates in the desired direction of rotation of the magnet.

3. A device according to claim 1, wherein the linkage comprises a screw and nut and the magnet is connected to the screw or nut via the gearbox to cause relative rotations, thereby extending the device.

4. A device according to claim 1, wherein there is a difference in the number of teeth between gears, thereby providing a reduction in the number of gears and space.

5. A device according to claim 1, wherein the gearbox has a gear ratio of 100:1 to 1000:1.

6. A device according to claim 1, wherein the two components are components of a prosthesis for fixing to a long bone.

7. A device according to claim 6, wherein the long bone is a femur.

8. An extendable endoprosthetic replacement device which comprises first and second components which are connected by a linkage of extendable length, the first component comprising a component of a limb joint and the second component having means for attachment to a resected long bone, a magnet connected to the linkage and means adapted for location externally of the patient for generating a moving electromagnetic field, thereby causing the magnet to rotate and the linkage to be extended wherein the magnet is connected to the linkage via a reduction gearbox having two or more gear reduction stages whereby the gearbox has a gear ratio of 100:1 or greater.

9. A device according to claim 8, wherein the first component comprises a component of a hip or knee joint.

10. A device according to claim 9, wherein the second component comprises a spigot adapted for fixing into the intermediary canal of a long bone.

11. A surgical distraction device for correcting curvature of the spine which comprises first and second extension rods, each having attachment means at one end for fixing to a respective vertebra, a linkage for linking the rods so that the ends carrying attachment means are relatively moveable, said linkage being connected to a drive mechanism comprising a rotatable magnet and a reduction gearbox having two or more gear reduction stages whereby the gearbox has a gear ratio of 100:1 or greater and actuating means for location externally of the patient for generating a moving or varying electric/magnetic field, thereby causing the magnet to rotate and the attachment means on one rod to move relatively to the attachment means on the other rod.

12. A device according to claim 11, wherein the actuating means is arranged to generate a rotating field which rotates in the desired direction of rotation of the magnet.

13. A device according to claim 11, wherein the linkage comprises a drive cog which engages with a worm encircling a rod so that movement of the worm causes the rod to extend lengthwise thereof.

\* \* \* \* \*